United States Patent [19]

Kiener

[11] Patent Number: 5,270,203
[45] Date of Patent: Dec. 14, 1993

[54] BIOLOGICALLY PURE CULTURE OF ALCALIGENES FAECALIS DSM 6335

[75] Inventor: Andreas Kiener, Visp, Switzerland

[73] Assignee: Lonza Ltd., Gampel/Valais, Switzerland

[21] Appl. No.: 903,765

[22] Filed: Jun. 25, 1992

Related U.S. Application Data

[62] Division of Ser. No. 850,801, Mar. 13, 1992.

[51] Int. Cl.$^5$ .......................... C12N 1/20; C12P 1/04; C12P 1/00
[52] U.S. Cl. ................... 435/252.1; 435/170; 435/41
[58] Field of Search ............... 435/252.1, 41, 170

[56] References Cited

U.S. PATENT DOCUMENTS

| | | | |
|---|---|---|---|
| 4,138,488 | 2/1979 | Sherlock et al. | 424/250 |
| 4,620,033 | 10/1986 | Isshiki et al. | 562/519 |
| 4,859,592 | 8/1989 | Hagedorn et al. | 435/122 |
| 5,013,656 | 5/1991 | Takayama et al. | 435/122 |
| 5,082,777 | 1/1992 | Lehky et al. | 435/122 |
| 5,089,411 | 2/1992 | Yamada et al. | 435/244 |
| 5,124,342 | 6/1992 | Kerdesky et al. | 514/369 |
| 5,135,858 | 8/1992 | Yamada et al. | 435/106 |
| 5,182,197 | 1/1993 | Kiener et al. | 435/122 |

FOREIGN PATENT DOCUMENTS

| | | | |
|---|---|---|---|
| 3343576 | 6/1985 | European Pat. Off. | 435/252.1 |
| 0152948 | 8/1985 | European Pat. Off. | |
| 187680 | 6/1988 | European Pat. Off. | |
| 0012978 | 1/1977 | Japan | 435/252.1 |
| 0220184 | 12/1984 | Japan | 435/252.1 |

OTHER PUBLICATIONS

Mauger J., et al., J. Biotech., vol. 8, No. 1, (May 1988), pp. 87 to 84.
Chemical Abstracts, vol. 88, No. 1, (Jan. 2, 1978), 2900j.
The Merck Index, 11th Ed., 1989, p. 1175, #7375, Picolinic Acid.
R. L. Tate and J. C. Ensign, Can. J. Microbiol. vol. 20, (1974), pp. 695 to 702.
G. Drews, Mikrobiologsches Praktikum (Microbiological Workshop), 4th Edition, (1983), Springer Verlag.
O. Shukla and S. M. Kaul, Indian J. of Biochemistry and Biophysics (1973), vol. 10, pp. 176 to 178.
O. Shukla et al., Indian J. of Biochemistry and Biophysics, vol. 14, (1977), pp. 292 to 295.

Primary Examiner—Douglas W. Robinson
Assistant Examiner—Deborah K. Ware
Attorney, Agent, or Firm—Fisher, Christen & Sabol

[57] ABSTRACT

The invention is a biologically pure culture of *Alcaligenes faecalis* DSM 6335. Furthermore, the culture or a mutant thereof, is capable of growing with 2-cyanopyridine as the sole carbon, nitrogen and energy source in order to produce 6-hydroxypicolinic acid. The specific reaction is the conversion of 2-cyanopyridine as the substrate into 6-hydroxypicolinic acid.

2 Claims, No Drawings

BIOLOGICALLY PURE CULTURE OF *ALCALIGENES FAECALIS* DSM 6335

This is a divisional application of Ser. No. 07/850,801, filed on Mar. 13, 1992 pending.

BACKGROUND OF THE INVENTION

1. Field of the Invention

The invention relates to a new microbiological process for the production of 6-hydroxypicolinic acid, starting from 2-cyanopyridine, as well as to new microorganisms suitable for the process.

2. Background Art

It is known that microorganisms of the genus Bacillus hydroxylate picolinic acid to 6-hydroxypicolinic acid [O. Shukla and S. M. Kaul, Indian J. of Biochemistry and Biophysics, (1973), Vol. 10, pages 176 to 178; O. Shukla et al., Indian J. of Biochemistry and Biophysics, Vol. 14, (1977), page 292 to 295]. A great drawback of this process is that the further metabolization of the 6-hydroxypicolinic acid can be stopped only with the inhibitor sodium arsenite, and, thus, the growth of the microorganisms also is inhibited. Another drawback is that 6-hydroxypicolinic acid is not exclusively formed, but instead a mixture of 3,6-dihydroxypicolinic acid and 6-hydroxypicolinic acid results.

R. L. Tate and J. C. Ension, Can. J. Microbiol., Vol. 20, (1974), pages 695 to 702, describes the hydroxylation of picolinic acid with microorganisms of the genus Arthrobacter. Drawbacks of this process are that these microorganisms cannot use picolinic acid exclusively as a carbon, nitrogen and energy source, but in the hydroxylation, a yeast extract has to be present, which can lead to undesirable impurities of the product. Another drawback lies in the fact that the 6-hydroxypicolinic acid is formed only in the case of low oxygen content, and the microorganisms are not present in the growth phase, and thus little product is formed.

BROAD DESCRIPTION OF THE INVENTION

The main object of the invention is to eliminate these drawbacks and to provide a simple, economical microbiological process for the production of 6-hydroxypicolinic acid starting from 2-cyanopyridine. An object of the invention is also to provide new microorganisms (biologically pure cultures thereof) useful in the new microbiologically process of the invention. Other objects and advantages of the invention are set out herein or are obvious herefrom.

The objects and advantages of the invention are achieved by the process and microorganisms of the invention.

The invention involves a microbiological process for the production of 6-hydroxypicolinic acid. The process includes biotransforming 2-cyanopyridine with certain microorganisms to 6-hydroxypicolinic acid and accumulating the latter in the medium. The microorganisms are those microorganisms that are capable of growing with 2-cyanopyridine as the sole carbon, nitrogen and energy source and of converting it as substrate to 6-hydroxypicolinic acid. Preferably the microorganism is *Alcaligenes faecalis* which has been deposited in the DSM with the deposit number 6335 (biologically pure cultures). The descendants and mutants thereof (biologically pure cultures) are also suitable. Preferably the effective enzymes of the microorganisms are induced with 2-cyanopyridine. Preferably the reaction takes place under (with) substrate addition once or continuously so that the substrate concentration does not exceed 20 percent by weight. Preferably the reaction is performed at a pH of 4 to 10 and a temperature of 10° to 50° C.

The invention also involves microorganisms (biologically pure or substantially biologically pure cultures) that are capable of growing with 2-cyanopyridine as the sole carbon, nitrogen and energy source and of converting it as the substrate to 6-hydroxypicolinic acid. Preferably the microorganism is *Alcaligenes faecalis* DSM 6335 (biologically pure or substantially biologically pure cultures). *Alcaligenes faecalis* DSM 6335 also is termed *Alcaligenes faecalis* Kie 31. The descendants and mutants thereof (biologically pure or substantially biologically pure cultures) are also suitable.

6-Hydroxypicolinic acid is used, for example, for the production of 2-oxypyrimidine [*Berichte der Deutschen Chemischen Gesellschaft*, (*Reports of the German Chemical Society*), 45, (1912), pages 2456 to 2467], which in turn is an important intermediate product for the production of pharmaceutical agents.

DETAILED DESCRIPTION OF THE INVENTION

According to the invention, all microorganisms are suitable that are capable of growing with 2-cyanopyridine as the sole carbon, nitrogen and energy source and of converting it as the substrate into 6-hydroxypicolinic acid. These microorganisms are a component of the invention and can be selected and isolated with the help of the usual microbiological techniques, for example, from sewage treatment plants, with 2-cyanopyridine as the growth substrate. The phrase "microorganisms which are capable of growing with 2-cyanopyridine as the sole carbon, nitrogen and energy source" comprises both mixtures of microorganisms and pure-isolates of the microorganisms, that can be used under sterile or nonsterile fermentation conditions.

Suitably, the microorganism *Alcaligenes faecalis* DSM 6335 and descendants and mutants thereof are used. The microorganism *Alcaligenes faecalis* DSM 6335 was deposited with the Deutschen Sammlong für Mikroorganismen und Zellkulturen GmbH [German Collection for Microorganisms and Cell Cultures GmbH] (DSM), Mascheroderweg 1b, D-3300 Brunswick, Germany, on Jan. 31, 1991 with the designation DSM No. 6335.

The scientific (taxonomic) description of *Alcaligenes faecalis* (DSM No. 6335) and properties of the strain are:

| cell shape | |
| --- | --- |
| width, micron | 0.5 to 0.8 |
| length, micron | 1.0 to 2.0 |
| mobility | + |
| flagella | peritrichous |
| gram reaction | − |
| lysis by 3 percent KOH | + |
| aminopeptidase (Cerny) | + |
| oxidase | + |
| catalase | + |
| growth | |
| anaerobic | − |
| 37°/40° C. | +/− |
| pH 5.6 | + |
| MacConkey broth (agar) | + |
| pigments | |
| nondiffusing | − |
| diffusing | − |
| fluorescent | − |

| -continued | |
|---|---|
| pyocyanine | − |
| acid from (OF test) | |
| aerobic glucose | − |
| anaerobic glucose | − |
| aerobic xylose | − |
| gas from glucose | − |
| acid from ASA* | |
| glucose | − |
| fructose | − |
| xylose | − |
| ONPG | − |
| ADH | − |
| LDC | − |
| indole | − |
| VP | − |
| $NO_2$ from $NO_3$ | − |
| denitrification | − |
| rods | |
| phenylalanine desaminase | − |
| levan from saccharose | − |
| lecithinase | − |
| urease | − |
| hydrolysis of starch | − |
| gelatin | − |
| casein | − |
| DNA | − |
| Tween 80 | − |
| aesculin | − |
| tyrosine catabolism | − |
| use of substrate | |
| acetate | + |
| adipate | − |
| azelate | − |
| caprate | + |
| citrate | + |
| glycolate | + |
| laevulinate | − |
| malate | + |
| malonate | + |
| mesaconate | − |
| phenylacetate | + |
| pimelate | − |
| sebacinate | − |
| D-tartrate | − |
| L-arabinose | − |
| fructose | − |
| glucose | − |
| mannose | − |
| maltose | − |
| xylose | − |
| ribose | − |
| mannitol | − |
| gluconate | − |
| 2-ketogloconate | − |
| N-acetylglucosamine | − |
| L-methionine | + |
| hydroxybenzoate | − |
| RESULT: Strain Kie 31 (DSM No. 6335) = *Alcaligenes faecalis* | |

*ASA = acetylsalicylic acid

The process for the production of 6-hydroxypicolinic acid is performed according to the invention in such a way that 2-cyanopyridine with one of the microorganisms of the invention is biotransformed to 6-hydroxypicolinic acid and the latter is accumulated in the medium.

Before the actual reaction, these microorganisms are usually cultivated (cultured) and the effective enzymes of the microorganisms are suitably induced with 2-cyanopyridine. Usually the cultivation (culture) and induction take place with 2-cyanopyridine in a concentration of 0.01 to 20 percent by weight, preferably in a concentration of 0.1 to 1 percent by weight. Then the microorganisms can be harvested either before the substrate addition (2-cyanopyridine) by the usual separation processes or the substrate (2-cyanopyridine) can be directly added to the microorganisms.

For the actual process, the cell suspension is then suitably adjusted to an optical density at 650 nm of 1 to 100, preferably to an optical density of 5 to 80. As the medium, those usual among experts can be used, preferably one of the media whose composition is given in Tables 1 and 2 below, is used. The substrate (2-cyanopyridine) for the production of 6- hydroxypicolinic acid can be added once or continuously. Suitably, the substrate addition takes place so that the substrate concentration in the medium does not exceed 20 percent by weight, preferably so that the substrate concentration does not exceed 10 percent by weight. Usually the reaction of 2-cyanopyridine to 6-hydroxypicolinic acid takes place with dormant cells. The pH of the reaction suitably is in a range of 4 to 10, preferably in a range of 5 to 9. Suitably the reaction is performed at a temperature of 10° to 50° C., preferably at a temperature of 20° to 40° C. After a usual reaction time of 1 to 100 hours, 6-hydroxypicolinic acid can be isolated, for example, by acidification of the cell-free fermentation solution.

EXAMPLE 1

Isolation Of 2-Cyanopyridine-Metabolizing Microorganisms

Aerobic 2-cyanopyridine-metabolizing microorganisms were concentrated in the A+N medium (see Table I below) with the addition of 0.1 percent (w/v) 2-cyanopyridine as the sole carbon and energy source. The general techniques for isolating microorganisms are described, for example, in G.Drews, Mikrobiologisches Praktikum (Microbiological Workshop), 4th edition, (1983), Springer Verlag. Samples from sewage treatment plants were used as an inoculum. The concentrations were cultivated in shaking flasks at 30° C. After inoculating three times in fresh medium, the concentrations were plated out on the same medium with the addition of 16 g of agar per liter and incubated at 30° C. After repeated plating-out on agar medium, pure cultures were able to be isolated.

TABLE 1

A + N Medium

| Composition | Concentration (mg/l) |
|---|---|
| $(NH_4)_2SO_4$ | 2000 |
| $Na_2HPO_4$ | 2000 |
| $KH_2PO_2$ | 1000 |
| NaCl | 3000 |
| $MgCl_2.6H_2O$ | 400 |
| $CaCl_2.2H_2O$ | 14.5 |
| $FeCl_3.6H_2O$ | 0.8 |
| pyridoxal hydrochloride | $10 \cdot 10^{-3}$ |
| riboflavin | $5 \cdot 10^{-3}$ |
| nicotinic acid amide | $5 \cdot 10^{-3}$ |
| thiamin hydrochloride | $2 \cdot 10^{-3}$ |
| biotin | $2 \cdot 10^{-3}$ |
| pantothenic acid | $5 \cdot 10^{-3}$ |
| p-aminobenzoate | $5 \cdot 10^{-3}$ |
| folic acid | $2 \cdot 10^{-3}$ |
| vitamin B12 | $5 \cdot 10^{-3}$ |
| $ZnSO_4.7H_2O$ | $100 \cdot 10^{-3}$ |
| $MnCl_2.4H_2O$ | $90 \cdot 10^{-3}$ |
| $H_3BO_3$ | $300 \cdot 10^{-3}$ |
| $CoCl_2.6H_2O$ | $200 \cdot 10^{-3}$ |
| $CuCl_2.2H_2O$ | $10 \cdot 10^{-3}$ |
| $NiCl_2.H_2O$ | $20 \cdot 10^{-3}$ |
| $Na_2MoO_4.H_2O$ | $30 \cdot 10^{-3}$ |
| $EDTANa_2.H_2O$ | $30 \cdot 10^{-3}$ |

TABLE 1-continued

| A + N Medium | |
|---|---|
| Composition | Concentration (mg/l) |
| $FeSO_4.H_2O$ | $2 \cdot 10^{-3}$ |

(The pH of the solution was adjusted to 7.0)

EXAMPLE 2

Reaction Of 2-Cyanopyridine To 6-Hydroxypicolinic Acid (a) *Alcaligenes faecalis* DSM No. 6335 (Kie 31) was cultivated in A+N medium (see Table 1 below) with the addition of 0.1 percent (w/v) 2-cyanopyridine in a fermenter at pH 7 and at a temperature of 30° C. Then the cells were centrifuged off, resuspended in A+N medium and adjusted to an optical density of 10 at 650 nm. This cell suspension was poured into a shaking flask and mixed with 0.1 mol/l (10.4 g/l) of 2-cyanopyridine. After an incubation of 16 hours at 30° C. on a shaking machine, 0.04 mol/l (5.5 g/l) of 6-hydroxypicolinic acid was able to be detected by analytical methods in the cell-free solution, which corresponded to a yield of 40 percent, relative to the 2-cyanopyridine used.

(b) *Alcaligenes faecalis* DSM No. 6335 was cultivated in a mineral salt medium (see Table 2 below) with addition of 0.1 percent (w/v) 2-cyanopyridine in a fermenter (working volume 5.5 liters) at pH 7 and a temperature of 30° C. 3 mol/l of sodium hydroxide and 8.5 percent (w/v) of phosphoric acid was used for the pH adjustment. During the growth, additional 2-cyanopyridine was added to the fermenter until after 24 hours of growth the optical density at 650 n was 5.1. Altogether 35 g of 2-cyanopyridine was metabolized during the growth phase. The microorganism suspension was mixed with 2-cyanopyridine (220 g) for the production of 6-hydroxypicolinic acid. After another incubation of 18 hours, 108 g of 6-hydroxypicolinic acid was isolated from the cell-free solution, corresponding to a yield of 37 percent relative to the 2-cyanopyridine used.

TABLE 2

| Composition Of The Mineral Salt Medium | |
|---|---|
| $MgCl_2.6H_2O$ | 0.8 g/l |
| $CaCl_2$ | 0.16 g/l |
| $Na_2SO_4$ | 0.25 g/l |
| $KH_2PO_4$ | 0.4 g/l |
| $Na_2HPO_4$ | 0.9 g/l |
| SLF | 1 ml/l |
| FeEDTA | 15 ml/l |
| Composition Of The Trace Elements (SLF) In The Mineral Salt Medium | |
| KOH | 15 g/l |
| $EDTANa_2.2H_2O$ | 100 g/l |
| $ZnSO_4.7H_2O$ | 9 g/l |
| $MnCl_2.4H_2O$ | 4 g/l |
| $H_3BO_3$ | 2.7 g/l |
| $CoCl_2.6H_2O$ | 1.8 g/l |
| $CuCl_2.2H_2O$ | 1.5 g/l |
| $NiCl_2.6H_2O$ | 0.18 g/l |
| $Na_2MoO_4.2H_2O$ | 0.2 g/l |
| Composition of FeEDTA | |
| $EDTANa_2.2H_2O$ | 5 g/l |
| $FeSO_4.7H_2O$ | 2 g/l |

(The pH of the solution was adjusted to 7.0.)

What is claimed is:

1. A biologically-pure culture of *Alcaligenes faecalis* DSM 6335, or a mutant thereof, which is capable of growing with 2-cyanopyridine as the sole carbon, nitrogen and energy source and of converting 2-cyanopyridine as the substrate into 6-hydroxypicolinic acid.

2. The biologically-pure culture according to claim 1 wherein said culture is of *Alcaligenes faecalis* DSM 6335.

* * * * *